United States Patent
Stein

(10) Patent No.: US 6,730,035 B2
(45) Date of Patent: May 4, 2004

(54) ULTRASONIC APPARATUS AND METHOD FOR PROVIDING QUANTITATIVE INDICATION OF RISK OF CORONARY HEART DISEASE

(75) Inventor: James H. Stein, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/290,421

(22) Filed: Nov. 7, 2002

(65) Prior Publication Data

US 2003/0229284 A1 Dec. 11, 2003

Related U.S. Application Data

(60) Provisional application No. 60/386,905, filed on Jun. 5, 2002.

(51) Int. Cl.[7] ................................................. A61B 8/00
(52) U.S. Cl. ........................................................... 600/449
(58) Field of Search ................................. 600/437, 443, 600/449, 453–456; 128/921–924

(56) References Cited

U.S. PATENT DOCUMENTS 6,132,373 A    10/2000    Ito et al.

OTHER PUBLICATIONS

Hodis, Howard N. et a l, "The Role of Carotid Arterial Intima–Media Thickness in Predicting Clinical Coronary Events" American College of Physicians Annals of Internal Medicine, Feb. 15, 1998 128:262–269.*

Schisterman, Enrique F., et al., Coronary Plaque as a Replacement for Age in the Framingham Risk Equation, 51st Annual Scientific Session, American College of Cardiology, Aug. 27, 2002.

Grundy, Scott M., Coronary Calcium as a Risk Factor: Role in Global Risk Assessment, Journal of American College of Cardiology, vol. 37, No. 6, 2001.

Grundy, Scott M., Coronary Plaque as a Replacement for Age as a risk Factor in Global Risk Assessment, Am J Cardiol 2001; 88(suppl):8E–11E.

* cited by examiner

*Primary Examiner*—Francis J. Jaworski
(74) *Attorney, Agent, or Firm*—Quarles & Brady LLP

(57) ABSTRACT

An ultrasound machine measures coronary intima-medial thickness and relates it to a statistically derived vascular age. Quantitative risk of coronary heart disease may be calculated using vascular age to substitute for chronological age in publicly available risk assessment data.

20 Claims, 2 Drawing Sheets

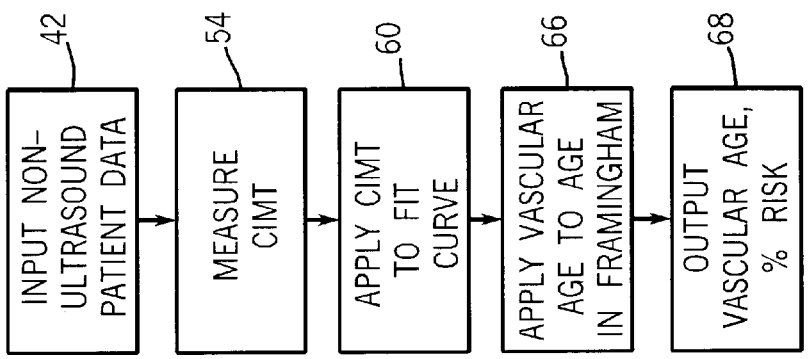
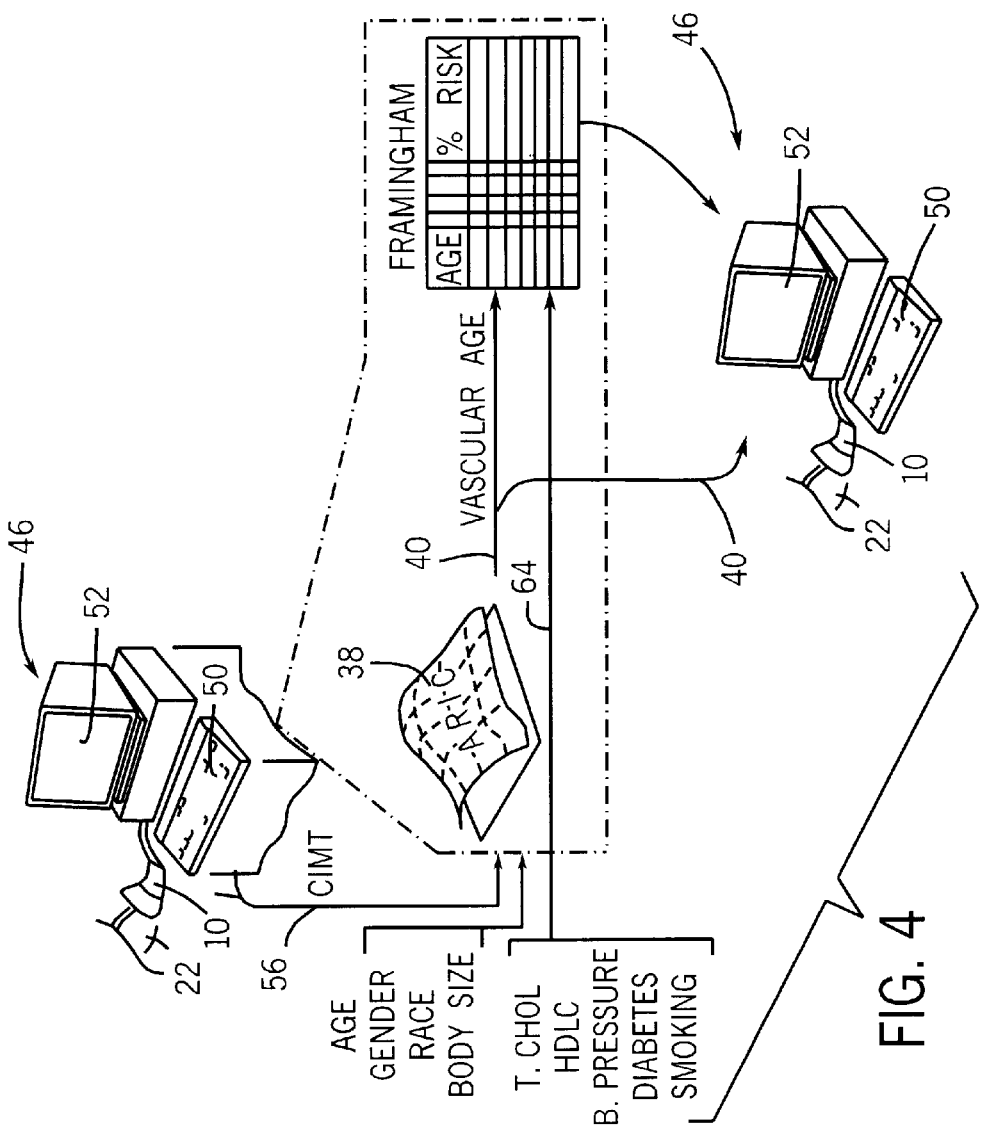

ULTRASONIC APPARATUS AND METHOD FOR PROVIDING QUANTITATIVE INDICATION OF RISK OF CORONARY HEART DISEASE

CROSS-REFERENCE TO RELATED APPLICATIONS

This application is based on provisional application No. 60/386,905 filed Jun. 5, 2002 and entitled "Mathematical Algorithms Allowing Determination of Vascular Age" and claims the benefit thereof.

STATEMENT REGARDING FEDERALLY SPONSORED RESEARCH OR DEVELOPMENT

This invention was made with United States government support awarded by the following agencies: NIH RR16176. The United States has certain rights in this invention.

BACKGROUND OF THE INVENTION

The present invention relates to ultrasonic medical equipment, and in particular, to a method employable with such equipment to assess risk of coronary heart disease (CHD).

A key challenge in healthcare is identifying individuals who are at high risk for CHD and who thus would be candidates for intensive medical intervention either in the form of additional diagnostic testing or the initiation of proven therapeutic strategies.

One method of assessing risk of coronary heart disease is the Framingham Global CHD Risk Assessment (henceforth the "Framingham Assessment"). See, "Prediction of Coronary Heart Disease Using Risk Factor Categories", *Circulation* 1998; 97: 1837–1847 Wilson et al.

The Framingham Assessment, based on a long-term study of a population of individuals, relates age, cigarette smoking, blood pressure, total cholesterol and high-density lipoprotein (HDL) cholesterol, and diabetes to a quantitative risk of CHD typically expressed in a percent chance of having a CHD event (heart attack or cardiac death) in ten years. A drawback to the Framingham Assessment is that age dominates all other risk factors even though the risks of coronary heart disease between individuals of the same age can differ substantially. The explanation for the relationship between age and CHD events most likely is increasing coronary plaque burden that occurs with advancing age. For this reason, it is generally recognized that a measure of coronary plaque burden might provide a better indicator of the probability of developing coronary heart disease for an individual than age alone.

There are a number of methods of measuring coronary plaque burden, including measurement of carotid intima-medial thickness (CIMT) with B mode ultrasound sonography. Such measurements provide a non-invasive and highly reproducible technique for quantifying sub-clinical atherosclerosis.

Measurement of CIMT is currently not used widely as a clinical tool, however. In part, this is because there is no established relationship between various patient factors, CIMT, and quantitative risk of cardiac heart disease. Ideally, the Framingham study would be repeated, but the age replaced by a CIMT measurement. Unfortunately, such studies take many years to complete and the future study is hampered by ethical concerns resulting from our understanding of the significance of some of the risk factors. For example, given the knowledge of the relationship between CHD and CIMT, long-term monitoring without treatment of patients with high CIMT may not be possible.

BRIEF SUMMARY OF THE INVENTION

The present inventors have recognized that a quantitatively rigorous relationship between CIMT and risk of CHD may be derived from the existing Framingham Assessment data by converting CIMT into an equivalent "vascular age" and substituting this "vascular age" for the chronological age used in the Framingham Assessment. The conversion of CIMT to vascular age can be done using studies that relate increase in CIMT to age in a standard population. One such study is the ARIC study described in "High Resolution B Mode Ultrasound Scanning Methods in the Arteriosclerosis Risk in Community Study (ARIC) *J. Neuroimaging*, 1991; 1:68–73, Bond et al.

These latter studies generally show a range of CIMT values for individuals of a given age within the population and thus cannot be used to relate CIMT to actual chronological age. Nevertheless, vascular age may be equated to the age of the study population at which the given individual's CIMT equals the population's mean or other statistical center value. The concept of vascular age allows connection between these two disparate studies, for example, that of the Framingham Assessment and ARIC, to provide a quantitative relationship between CIMT and risk of coronary heart disease.

Specifically then, the present invention provides an ultrasonic diagnostic machine having an ultrasonic transducer that is positionable near the carotid artery to obtain echo signals from the carotid artery. A processing circuit communicating with the ultrasound transducer operates to process the echo signal to review the carotid intima-medial thickness (CIMT) and to apply the revealed CIMT to stored data relating CIMT of a population to a quantified risk of coronary heart disease (CHD). This quantified risk of heart disease is then output.

Thus, it is one object of the invention to provide the quantitative relationship between CIMT and risk of CHD such as may guide selection of treatment regimens.

The stored data used by the ultrasound machine may combine first data relating the CIMT to a vascular age and second data relating vascular age to quantified risk of CHD. The first data may be the ARIC data and the second data may be the data of the Framingham Assessment.

Thus, it is another object of the invention to establish a relationship between CIMT and risk of CHD using pre-existing studies.

The first data may relate multiple CIMT values to a given age but may be used to provide a single vascular age from a single CIMT value by a mathematical or statistical curve fitting process.

Thus, it is another object of the invention to employ existing studies describing CIMT as a function of age to create a virtual study relating CIMT values to vascular age.

The processing circuit may provide for input of patient data selected from the group consisting of: chronological age, gender, race, and body size. At least one of these patient data may also be applied to at least one of the first and second data sets.

Thus, it is another object of the invention to take advantage of the other patient input factors that may be used along with CIMT to establish quantified risk of CHD.

In one embodiment of the invention, the output from the ultrasound diagnostic machine may be vascular age.

Thus, it is another object of the invention to provide a simple unit for assessing CIMT data that can be readily understood by physicians and patients.

These particular objects and advantages may apply to only some embodiments falling within the claims and thus do not define the scope of the invention.

BRIEF DESCRIPTION OF THE DRAWINGS

FIG. 4 is a data flow diagram showing collection of CIMT data obtained from an ultrasound machine together with other patient data and conversion of this data to vascular age by use of a surface derived from the ARIC data of FIG. 3; and the further use of the vascular age, both as direct output to the physician and as an input to the Framingham Assessment to provide a quantitative measurement of risk of CHD;

FIG. 5 is a flow chart showing the steps of FIG. 4;

DETAILED DESCRIPTION OF THE PREFERRED EMBODIMENT

Figure 1:
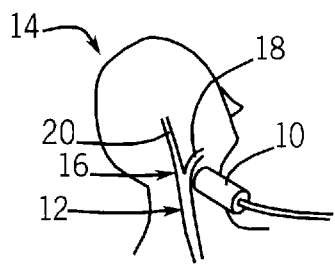
FIG. 1 is a perspective view of a patient's head showing the carotid artery and the proper positioning of an ultrasonic transducer for the measurements used in the present invention.

Referring now to FIG. 1, an ultrasound probe 10 may be directed toward the common carotid artery 12 of a patient 14 near the branching or bifurcation 16 of the carotid artery 12 into internal carotid artery 18 and exterior carotid artery 20. The ultrasound transducer may, for example, be an 8-megahertz linear array vascular ultrasound transducer (8L5) sold by Acuson of Mountain View, Calif. for use with the Acuson Sequoia ultrasound machine, or a similar transducer made by another vendor.

Figure 2:
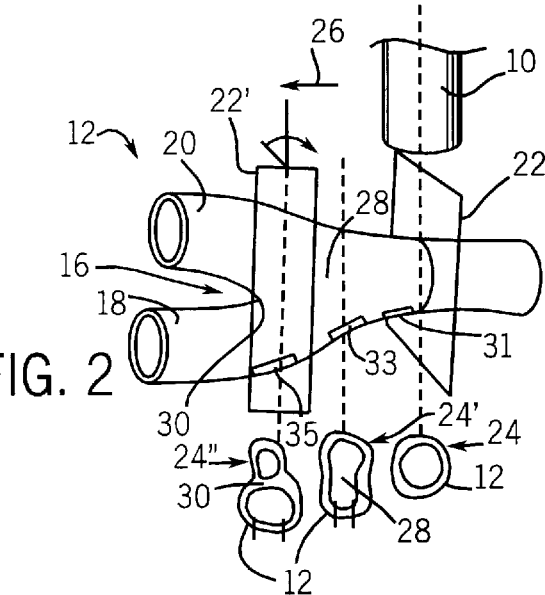
FIG. 2 is a fragmentary enlarged view of a bifurcation of the carotid artery used to locate positions for measurement of CIMT.

As shown in FIG. 2, the ultrasound probe 10 may be directed to transmit a generally planar beam 22, defining a coplanar image plane, that is perpendicular to the lumen of the carotid artery 12 to provide a generally ring-shaped cross-sectional image 24 of a single lumen before the bifurcation 16. The planar beam 22 is established to be essentially perpendicular to the axis of the lumen by adjusting the angle to increase the sharpness of the walls of the cross sectional image 24.

The ultrasound probe 10 may then be moved in a superior direction 26 past the general enlargement of the carotid artery into a bulb 28, shown in cross sectional image 24', to continue to the carotid bifurcation 16 characterized by the presence of a flow divider 30 and two lumens as indicated by cross sectional image 24". At this time, the ultrasound probe 10 may be rotated about its axis ninety degrees producing planar beam 22' to provide a cross section parallel to the lumen encompassing three locations along a distal wall of the carotid artery 12.

The three locations include a common segment 31 defined as the distal one centimeter of the carotid artery 12 immediately proximal to the onset of increased spatial separation of the walls of the common carotid artery (i.e., immediately before the origin of the bulb 28), the bifurcation segment 33 defined as the distal one centimeter of the bulb 28 characterized by the presence of the flow divider 30 between the interior carotid arteries 18 and exterior carotid arteries 20 and the internal segment 35 defined as the proximal one centimeter of the internal carotid artery 18 starting immediately beyond the flow divider 30. At each of these segments 31, 33, and 35, the thickness of the intimal and medial layers of the distal walls is measured. Alternatively, images of the far wall (or near wall if normative values are available) can be obtained at multiple, predefined, protocol-specified interrogation angles.

The combined thickness of the intimal and medial layers can be measured using, for example, software commercially available from Freeland Systems of Indianapolis, Ind., under the trade name Access Point 2000, or similar software such as that available from Camtronics, Inc., Hartland, Wis. A composite CIMT value may then be calculated as a mean of the averages or means of each of these segments according to the standardized protocol from the ARIC study.

Figure 3:
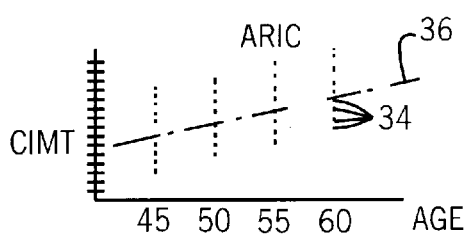
FIG. 3 is a graph showing in simplified representation the ARIC data such as provides a range of CIMT values for different age groups within the ARIC population and showing a curve fitted to this data to deduce a vascular age from CIMT.

Referring now to FIG. 3, the ARIC study established a relationship between CIMT and age (and gender and race) indicated by scatter plots points 34 reflecting the fact that in the populations studied in the ARIC study individuals of the same given age had different CIMT values varying over a substantial range. Generally, therefore, a given CIMT value cannot be mapped to a particular age using the ARIC data.

In order to overcome this problem, a curve 36 is fit to these scatter plot points 34 to provide a best fit. A number of different best-fit criteria are possible, with a linear regression being used in the preferred embodiment.

Vascular age can be determined by linear regression modeling using published nomograms of CIMT percentiles ($5^{th}$, $10^{th}$, $25^{th}$, $50^{th}$, $75^{th}$, $90^{th}$, and $95^{th}$) according to chronological age, sex, and race. Linear regression models are first constructed for each of the CIMT percentile functions for each carotid arterial segment 31, 33, and 35: by sex (male and female), race (white and black), and age (5-year increments from 45–65 years old). Composite CIMT values can then be used to determine the vascular age defined as the age at which the composite CIMT value for an individual of a given race and sex would represent the median value ($50^{th}$ percentile).

Specifically, the linear $50^{th}$ percentile function by chronological age, sex, and race can be used to assign a vascular age to the subject having a given composite CIMT value such that if each of the subject's segmental scores were at the $50^{th}$ percentile for their chronological age, sex, and race, then their composite CIMT would be at the $50^{th}$ percentile and their vascular age would be equal to their chronological age. For example, a 45-year black female with a composite CIMT of 0.593 mm would have a CIMT percentile of 50% and a vascular age of 50 years; however, a 45-year black female with a composite CIMT of 0.678 mm would have a CIMT percentile of 71% and a vascular age of 55 years, representing the age at which a composite CIMT value of 0.678 mm represents the $50^{th}$ percentile.

Using this modeling, a given CIMT value may be mapped to a unique vascular age. It should be noted that vascular age will generally not match the chronological age of the patient 14 but will be a statistical construction in which the vascular age of the patient 14 is an age of ARIC data at which the patient's CIMT is near the middle of the range of the scatter plot points 34.

Referring now to FIG. 4, the linear regression curve 36 as extended across other patient variables of the ARIC study such as age, gender, and race and potentially across new variables such as body size creates a multidimensional surface 38 mapping values of the patient variables to a unique vascular age 40. As a practical matter, the surface 38 may be stored as one or more data table and vascular age may be determined by interpolation between data table values as is well understood in the art.

Referring now to FIG. 5, a first step of the present invention indicated by process block 42 collects the patient data described above including, for example, age, gender, race and body size. This information may be entered into an ultrasound machine 46 by means of a keyboard 50 or the data may be directly imported from the ultrasound machine into a software program and displayed on a display 52 according to techniques well known in the art.

At process block 54, the above-described CIMT measurement is performed using the ultrasound probe 10.

The CIMT data 56 and the patient data 58 form arguments that are applied to the N-dimensional surface 38 to produce a vascular age 40 as indicated by process block 60. This determination of vascular age of process block 60 may be performed by processing circuitry contained in the ultrasound machine 46, however, it is also contemplated that the vascular age may be computed by a separate computing device.

The vascular age 40 may then be output to the display 52 of the ultrasound machine 46 to provide an intuitive measure of CIMT. Generally, the patient will compare his or her vascular age to his or her actual chronological age to get a sense of his or her risk of coronary heart disease.

The ultrasound machine 46 or the separate computing device may store the Framingham Assessment data 62 providing inputs for chronological age as well as inputs for cholesterol, HDL cholesterol, smoking, total cholesterol and diabetes. As represented by process block 66, these latter five inputs 64 are then applied to the Framingham Assessment data 62 with the vascular age 40 being substituted for the chronological age expected from the Framingham analysis. This application of data generally involves finding a row in the Framingham Assessment data 62 matching each of the characteristics or most closely matching each of inputs 64 and vascular age 40.

The Framingham Assessment data 62 then yields a percent risk of CHD according to this well-known study. This risk is output as indicated by process block 68.

The present invention thus allows the inputting of the CIMT as well as other information such as age, gender, and race data into the Framingham study through the use of the concept of vascular age.

Figure 6:
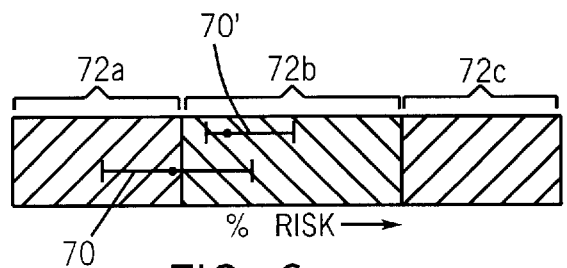
FIG. 6 is a graph showing treatment options that may depend on a quantifiable risk of heart disease and showing uncertainty in the Framingham study for an individual as may be reduced by the present invention.

Referring now to FIG. 6, although the Framingham Assessment accurately reflects risk of CHD for a population, or an individual, it will provide an uncertainty 70 measurable in a range of percent risk of CHD. This uncertainty may span ranges of risk 72A, 72B and 72C associated with different treatment options. It is expected that use of the present invention will reduce the uncertainty as indicated by 70' thereby clarifying treatment options. This expected improvement may be established by obtaining additional information from the ARIC study indicating whether individuals in that study had a clinical manifestation of coronary heart disease in the period following their measurement. The results obtained by the present invention would then be compared to actual outcomes of the ARIC population to confirm clinical significance.

Figure 7:
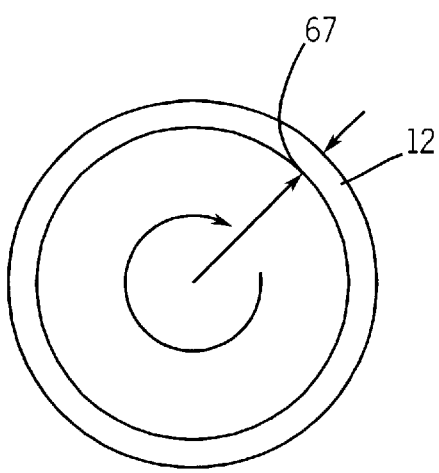
FIG. 7 is a cross-sectional view of the artery of FIG. 2 showing an alternative measurement of CIMT possible with 3-D ultrasound machines.

Referring now to FIG. 7, the present invention is not limited to two dimensional ultrasound machines but may find application in three dimensional ultrasound machines which collect a volume of ultrasonic data and can display a cross-sectional image of the carotid artery 12. In this case, the intima-medial separation 67 may be measured, for example, in a ring extending circumferentially around the carotid artery in a plane perpendicular to the lumen of the artery rather than in a line segment along the distal portion of the lumen as described above. The measurements taken in the ring can be averaged together and substituted for the measurements described with respect to FIG. 2. Three rings may be measured intersecting the common section 31, the bifurcation segment 33, and the internal segment 35.

While one embodiment of the present invention contemplates that the measurement of CIMT will be performed manually, in an alternative embodiment the measurements of CIMT may be performed automatically by the ultrasound machine 36 which may also perform the averaging necessary for the software described. Such automatic measuring is known in the art and is described, for example, in U.S. Pat. No. 6,132,373 issued Oct. 17, 2000 hereby incorporated by reference.

Figure 8:
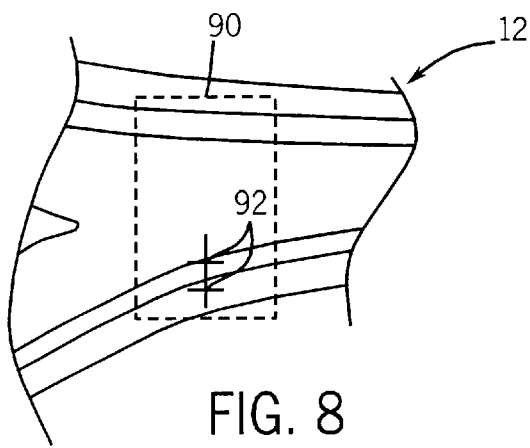
FIG. 8 is a figure showing a display of a B mode ultrasound image of the artery of FIG. 2 together with display of a region of interest and cursor ruler lines for automatic CIMT measurement.

Referring to FIG. 8, alternatively a combination of manual and automatic measurement techniques may be used in which an operator of the ultrasound machine 46 locates a region of interest cursor 90 being generally a rectangle over the image of the carotid artery 12 displayed on the display 52. The region of interest cursor 90 allows the operator to identify the appropriate regions (common section 31, the bifurcation segment 33, and the internal segment 35.). Once the region of interest cursor is located, defining the length along the wall of the carotid artery 12, thickness cursors 92 may be placed on either side of the intimal and medial layers of the distal wall at a particular location. The CIMT value may then be automatically computed based on starting points of the thickness cursors 92 extrapolated by computer analyses of the image data using region extraction algorithms well known in the art.

It is specifically intended that the present invention not be limited to the embodiments and illustrations contained herein, but include modified forms of those embodiments including portions of the embodiments and combinations of elements of different embodiments as come within the scope of the following claims.

I claim:

1. A diagnostic ultrasound machine comprising:
   an ultrasonic transducer positionable near the carotid artery to obtain echo signals from the carotid artery;
   a processing circuit communicating with the ultrasonic transducer and operating to:
   (i) process the echo signal to reveal carotid intima-medial thickness (CIMT);
   (ii) apply the revealed CIMT to stored first data relating the CIMT to vascular age to determine vascular age
   (iii) apply the determined vascular age to stored second data relating vascular age to the quantified risk of heart disease, and
   (iv) output the quantified of risk of heart disease.

2. The diagnostic ultrasonic machine of claim 1 wherein the first data is derived from data relating age to CIMT in a study population.

3. The diagnostic ultrasonic machine of claim 2 wherein the data relating age to CIMT is ARIC data.

4. The diagnostic ultrasonic machine of claim 2 wherein multiple CIMT values related to a single age are combined by curve fitting to yield a single vascular age for a single CIMT value.

5. The diagnostic ultrasonic machine of claim 1 wherein the second data is data relating chronological age to quantified risk of heart disease and wherein the first and second data are combined by taking vascular age deduced from the first data set and inputting it as chronological age into the second data set.

6. The diagnostic ultrasonic machine of claim 5 wherein the second data is Framingham data.

7. The diagnostic ultrasonic machine of claim 1 wherein the processing circuit further provides for input of patient data selected from the group consisting of: chronological age, gender, race and body size and wherein at least one of these patient data are also applied to at least one of the first and second data sets.

8. The diagnostic ultrasonic machine of claim 1 wherein the measure of risk of heart disease is expressed in percent chance of heart disease within ten years.

9. The diagnostic ultrasonic machine of claim 1 wherein the measure of CIMT is an average of carotid intima-medial thickness over a predetermined region of the carotid artery.

10. The diagnostic ultrasonic machine of claim 9 wherein the predetermined region is near the carotid bifurcation.

11. The diagnostic ultrasonic machine of claim 9 wherein the predetermined region is an axial line along the carotid artery.

12. The diagnostic ultrasonic machine of claim 1 wherein the processing circuitry collects a three-dimensional image set of the carotid artery and wherein the predetermined region is a circumferential ring of the carotid artery.

13. The diagnostic ultrasonic machine of claim 1 wherein the processing circuitry provides automatic measurement of the CIMT.

14. The diagnostic ultrasonic machine of claim 1 wherein the processing circuitry further output an image of the carotid artery and accepts user input locating points on the image for the automatic measurement.

15. A diagnostic ultrasound machine comprising:
    an ultrasonic transducer positionable near the carotid artery to obtain echo signals from the carotid artery;
    a processing circuit communicating with the ultrasonic transducer and operating to:
        (i) process the echo signal to reveal carotid intima-medial thickness (CIMT);
        (ii) apply the revealed CIMT to stored data relating CIMT of a population to a vascular age indicating statistical derived age of an individual having the revealed CIMT in a standard population; and
        (iii) output the vascular age.

16. The diagnostic ultrasonic machine of claim 15 wherein the stored data is derived from data relating age to CIMT in a study population.

17. The diagnostic ultrasonic machine of claim 16 wherein the data relating age to CIMT is ARIC data.

18. The diagnostic ultrasonic machine of claim 16 wherein multiple CIMT values related to a single age are combined by curve fitting to yield a single vascular age for a single CIMT value.

19. The diagnostic ultrasonic machine of claim 15 wherein the processing circuit further provides for input of patient data selected from the group consisting of: chronological age, gender, race and body size and wherein at least one of these patient data are also applied to the stored data.

20. A method of deducing a quantified risk of heart disease for an individual having a given chronological age and a given carotid intima-medial thickness (CIMT) comprising the steps of:
    (a) deducing a vascular age of the individual differing from the given chronological age such as would place the individual's given CIMT in a median of CIMT for that vascular age for a standard population;
    (b) using the vascular age as an input for chronological age in a Framingham model of heart disease to provide an estimate of cardiac heart disease; and
    (c) providing the individual with the vascular age and estimate of cardiac heart disease.

* * * * *